(12) United States Patent
Jin et al.

(10) Patent No.: US 9,064,033 B2
(45) Date of Patent: *Jun. 23, 2015

(54) INTELLIGENT DECISION SUPPORT FOR CONSENT MANAGEMENT

(75) Inventors: Hongxia Jin, San Jose, CA (US); Scott Schumacher, Porter Ranch, CA (US); Qihua Wang, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 548 days.

This patent is subject to a terminal disclaimer.

(21) Appl. No.: 13/176,011

(22) Filed: Jul. 5, 2011

(65) Prior Publication Data

US 2013/0014278 A1   Jan. 10, 2013

(51) Int. Cl.
  *G06F 7/04* (2006.01)
  *G06F 19/00* (2011.01)

(52) U.S. Cl.
  CPC .................................. *G06F 19/322* (2013.01)

(58) Field of Classification Search
  CPC ... G06F 19/322; G06F 19/32; H04L 12/2461; H04L 29/06632; H04L 29/06823
  USPC .......................................................... 726/28
  See application file for complete search history.

(56) References Cited

U.S. PATENT DOCUMENTS

| | | | |
|---|---|---|---|
| 6,289,462 B1* | 9/2001 | McNabb et al. | 726/21 |
| 6,408,336 B1* | 6/2002 | Schneider et al. | 709/229 |
| 7,788,040 B2 | 8/2010 | Haskell et al. | |
| 2002/0188869 A1* | 12/2002 | Patrick | 713/201 |
| 2003/0159070 A1* | 8/2003 | Mayer et al. | 713/201 |
| 2004/0039734 A1* | 2/2004 | Judd et al. | 707/3 |
| 2004/0143457 A1 | 7/2004 | Demirian et al. | |
| 2005/0222876 A1 | 10/2005 | Iwayama et al. | |
| 2008/0103829 A1 | 5/2008 | Mankopf et al. | |
| 2010/0138902 A1 | 6/2010 | Shelton | |
| 2010/0250285 A1* | 9/2010 | Shelton | 705/3 |
| 2011/0055897 A1* | 3/2011 | Arasaratnam | 726/3 |

OTHER PUBLICATIONS

Breitenstein, A., "U.S. Health Information Privacy Policy: Theory and Practice," Personal Medical Information: Security, Engineering & Ethics, pp. 209-224, 1997.
Aich et al., "Role Based Access Control With Spatiotemporal Context for Mobile Applications," Transactions on Computational Science, IV, pp. 177-199, 2009.
"Public Access to Health Information: Finding a Balance—An MLA & AAHSL Perspective," May 2003.
National Institutes of Health, "Access to Health Information of Individuals," National Library of Medicine, May 2004.
Department of Health, "Access to Patient Information," Library of the Department of Health, 1989, Revised Jun. 1989.
Intersystems Corporation, The Requirements of Health Information Exchanges—and How Intersystems Technology Addresses Them, 2010.
Intersystems Corporation, "The Requirements of Health Information Exchanges—and How HealthShare Addresses Them," 2010.

* cited by examiner

*Primary Examiner* — Esther B Henderson
(74) *Attorney, Agent, or Firm* — Lieberman & Brandsdorfer, LLC

(57) ABSTRACT

Embodiments of the invention relate to a system and computer program product to intelligently provide consent to access a record in a shared pool of resources. Tools are provided to support policies to address and maintain restrictive access of a designated record, both with respect to local and non-local rules and regulations, as well as personal restrictions pertaining to personal and discretionary sharing decisions.

12 Claims, 11 Drawing Sheets

INTELLIGENT DECISION SUPPORT FOR CONSENT MANAGEMENT

BACKGROUND

This invention relates to a quantitative approach for consent management to confidential data. More specifically, the invention relates to access to patient medical records and employing analytical techniques to assist patient in making access control decisions.

Cloud computing is a model of service delivery for enabling convenient, on-demand network access to a shared pool of configurable computer resources, e.g. networks, network bandwidth, servers, processing, memory, storage, applications, virtual machines, and services, that can be rapidly provisioned and released with minimal management effort or interaction with a provider of service. One of the characteristics of cloud computing infrastructure is that applications can be launched from a plurality of locations and shared with multiple users. More specifically, the cloud computing infrastructure offers a collaboration system that may serve multiple clients from different organizations. Medical providers are starting to store and transmit patient medical records in electronic form, and in some embodiments to the shared pool of computer resources. Regional and nationwide health information exchange (HIE) systems are emerging within the cloud computing environment where patient medical records from different sources may be assessed in a centralized manner.

Although there is a convenience factor associated with the availability of patient medical records in the cloud computing environment, health information security is a concern. Specifically, abuse of data associated with patient medical records or security breaches on the system may lead to compromising patient privacy. As such, a security system must be employed within the system to ensure trust as health information technology systems become ubiquitous.

BRIEF SUMMARY

This invention comprises a system and article for automatic decision support for patient consent management and mitigation of data leakage in a healthcare medical record/file sharing environment.

In one aspect, a computer program product is delivered as a service through a network connection. The computer program product comprises a computer readable storage medium having computer readable program code embodied therewith. Computer readable program code is configured to receive an access request for a record, and to identify information associated with both the record, including the record type, and the access request, including the identity of a requestor and a purpose associated with the access request. In response to the request and associated identification, computer readable program code is provided to compute the following measurements for the access request: an importance measurement, a sensitivity measurement, and a relevance measurement. More specifically, the relevance measurement determines a mathematical value associated with any previous requests for the same purpose for the identified record type. Based upon the measurements, computer readable program code is provided to compute a consent recommendation based upon the computed importance, sensitivity, and relevance measurements. The consent recommendation for the record access request includes either a grant or denial of access to the requested record.

In a further aspect, a system is provided with tools to support consent management of a private record. A storage component is provided in the system to store data in the form of a record and information describing an access control policy to the record. In addition, a functional unit is provided in communication with the storage component. The functional unit includes tools to support consent management, including an access manager, a measurement manager, and a consent manager. The access manager is configured to receive an access request for the record, with the access request including a record type, an identity of a requestor, and a purpose associated with the access request. The measurement manager is configured to compute the following elements associated with the access request: an importance measurement, a sensitivity measurement, and a relevance measurement. A consent manager is provided in communication with the measurement manager, with the consent manager configured to compute a consent recommendation based upon the measurements computed by the measurement manager. A decision to either grant or deny access to the requested record is provided based upon the consent recommendation of the consent manager.

Other features and advantages of this invention will become apparent from the following detailed description of the presently preferred embodiment of the invention, taken in conjunction with the accompanying drawings.

BRIEF DESCRIPTION OF THE SEVERAL VIEWS OF THE DRAWINGS

The drawings referenced herein form a part of the specification. Features shown in the drawings are meant as illustrative of only some embodiments of the invention, and not of all embodiments of the invention unless otherwise explicitly indicated.

DETAILED DESCRIPTION

Figure 1:
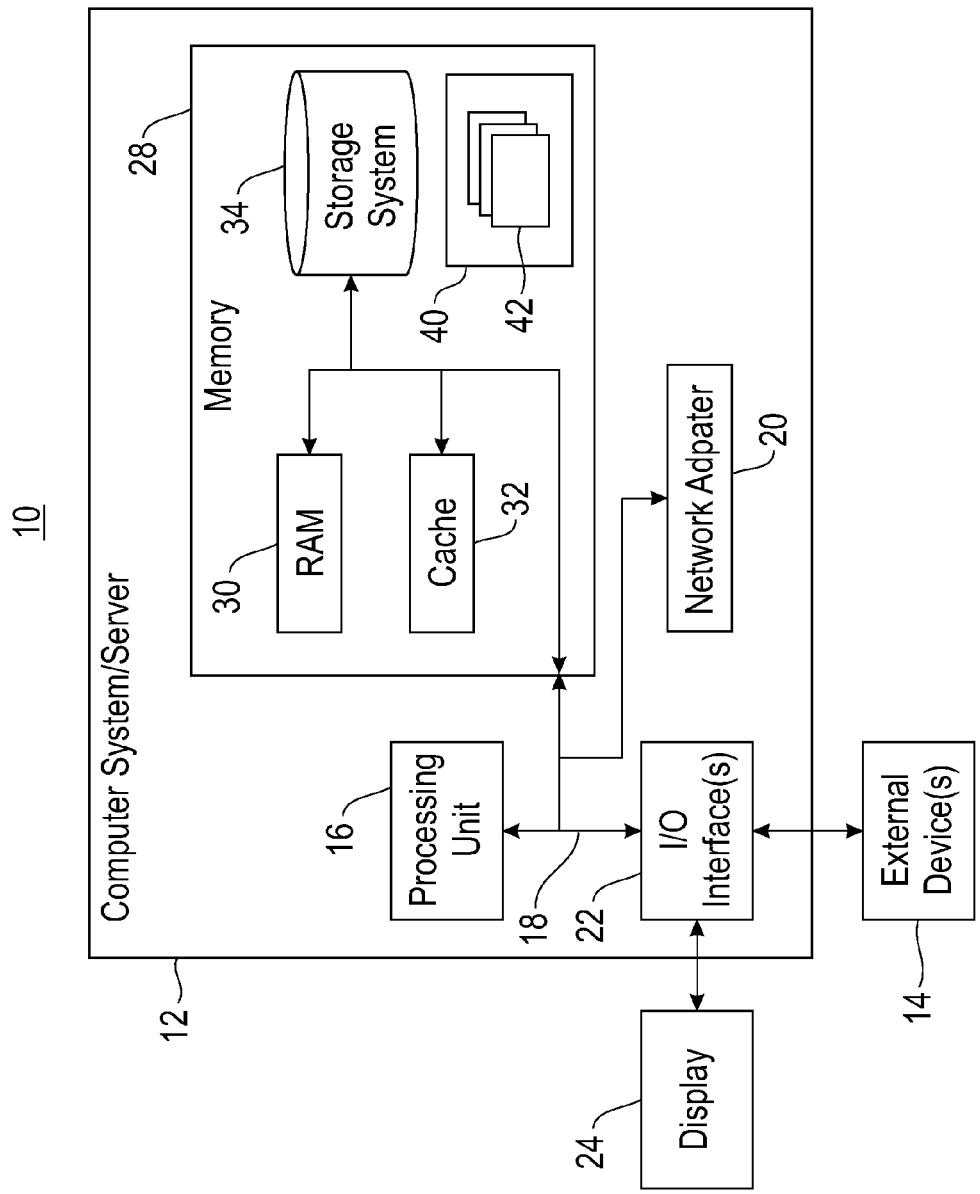
FIG. 1 depicts a cloud computing node according to an embodiment of the present invention.

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

The functional unit(s) described in this specification has been labeled with tools in the form of managers. A manager may be implemented in programmable hardware devices such as field programmable gate arrays, programmable array logic, programmable logic devices, or the like. The managers may also be implemented in software for processing by various types of processors. An identified manager of executable code may, for instance, comprise one or more physical or logical blocks of computer instructions which may, for instance, be organized as an object, procedure, function, or other construct. Nevertheless, the executables of an identified manager need not be physically located together, but may comprise disparate instructions stored in different locations which, when joined logically together, comprise the managers and achieve the stated purpose of the managers.

Indeed, a manager of executable code could be a single instruction, or many instructions, and may even be distributed over several different code segments, among different applications, and across several memory devices. Similarly, operational data may be identified and illustrated herein within the manager, and may be embodied in any suitable form and organized within any suitable type of data structure. The operational data may be collected as a single data set, or may be distributed over different locations including over different storage devices, and may exist, at least partially, as electronic signals on a system or network.

Reference throughout this specification to "a select embodiment," "one embodiment," or "an embodiment" means that a particular feature, structure, or characteristic described in connection with the embodiment is included in at least one embodiment of the present invention. Thus, appearances of the phrases "a select embodiment," "in one embodiment," or "in an embodiment" in various places throughout this specification are not necessarily referring to the same embodiment.

Furthermore, the described features, structures, or characteristics may be combined in any suitable manner in one or more embodiments. In the following description, numerous specific details are provided, such as examples of an application manager, a replication manager, a migration manager, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of devices, systems, and processes that are consistent with the invention as claimed herein.

A cloud computing environment is service oriented with a focus on statelessness, low coupling, modularity, and semantic interoperability. At the heart of cloud computing is an infrastructure comprising a network of interconnected nodes. Referring now to FIG. 1, a schematic of an example of a cloud computing node is shown. Cloud computing node (10) is only one example of a suitable cloud computing node and is not intended to suggest any limitation as to the scope of use or functionality of embodiments of the invention described herein. Regardless, cloud computing node (10) is capable of being implemented and/or performing any of the functionality set forth hereinabove. In cloud computing node (10) there is a computer system/server (12), which is operational with numerous other general purpose or special purpose computing system environments or configurations. Examples of well-known computing systems, environments, and/or configurations that may be suitable for use with computer system/server (12) include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server (12) may be described in the general context of computer system-executable instructions, such as program modules, being executed by a computer system. Generally, program modules may include routines, programs, objects, components, logic, data structures, and so on that perform particular tasks or implement particular abstract data types. Computer system/server (12) may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server (12) in cloud computing node (10) is shown in the form of a general-purpose computing device. The components of computer system/server (12) may include, but are not limited to, one or more processors or processing units (16), a system memory (28), and a bus (18) that couples various system components including system memory (28) to processor (16). Bus (18) represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer system/server (12) typically includes a variety of computer system readable media. Such media may be any available media that is accessible by computer system/server (12), and it includes both volatile and non-volatile media, removable and non-removable media.

System memory (28) can include computer system readable media in the form of volatile memory, such as random access memory (RAM) (30) and/or cache memory (32). Computer system/server (12) may further include other removable/non-removable, volatile/non-volatile computer system storage media. By way of example only, storage system (34) can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus (18) by one or more data media interfaces. As will be further depicted and described below, memory (28) may include at least one program product having a set (e.g., at least one) of program modules that are configured to carry out the functions of embodiments of the invention.

Program/utility (40), having a set (at least one) of program modules (42), may be stored in memory (28) by way of example, and not limitation, as well as an operating system, one or more application programs, other program modules, and program data. Each of the operating systems, one or more application programs, other program modules, and program data or some combination thereof, may include an implementation of a networking environment. Program modules (42) generally carry out the functions and/or methodologies of embodiments of the invention as described herein.

Computer system/server (12) may also communicate with one or more external devices (14), such as a keyboard, a pointing device, a display (24), etc.; one or more devices that enable a user to interact with computer system/server (12); and/or any devices (e.g., network card, modem, etc.) that enable computer system/server (12) to communicate with one or more other computing devices. Such communication can occur via Input/Output (I/O) interfaces (22). Still yet, computer system/server (12) can communicate with one or more networks such as a local area network (LAN), a general wide area network (WAN), and/or a public network (e.g., the Internet) via network adapter (20). As depicted, network adapter (20) communicates with the other components of computer system/server (12) via bus (18). It should be understood that although not shown, other hardware and/or software components could be used in conjunction with computer system/server (12). Examples, include, but are not limited to: microcode, device drivers, redundant processing units, external disk drive arrays, RAID systems, tape drives, and data archival storage systems, etc.

Figure 2:
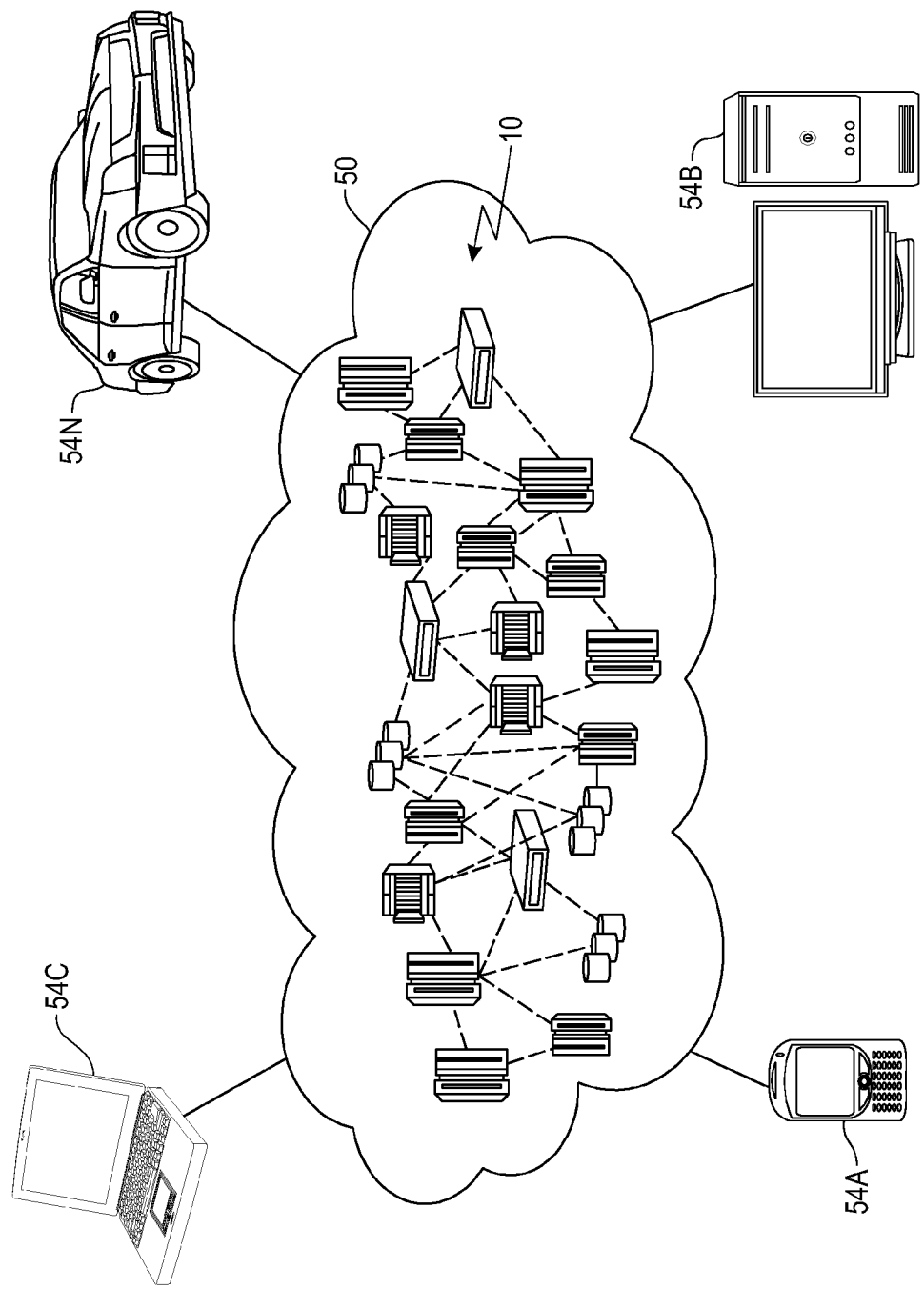
FIG. 2 depicts a cloud computing environment according to an embodiment of the present invention.

Referring now to FIG. 2, illustrative cloud computing environment (50) is depicted. As shown, cloud computing environment (50) comprises one or more cloud computing nodes (10) with which local computing devices used by cloud consumers, such as, for example, personal digital assistant (PDA) or cellular telephone (54A), desktop computer (54B), laptop computer (54C), and/or automobile computer system (54N) may communicate. Nodes (10) may communicate with one another. They may be grouped (not shown) physically or virtually, in one or more networks, such as Private, Community, Public, or Hybrid clouds as described hereinabove, or a combination thereof. This allows cloud computing environment (50) to offer infrastructure, platforms and/or software as services for which a cloud consumer does not need to maintain resources on a local computing device. It is understood that the types of computing devices (54A)-(54N) shown in FIG. 2 are intended to be illustrative only and that computing nodes (10) and cloud computing environment (50) can communicate with any type of computerized device over any type of network and/or network addressable connection (e.g., using a web browser).

Figure 3:
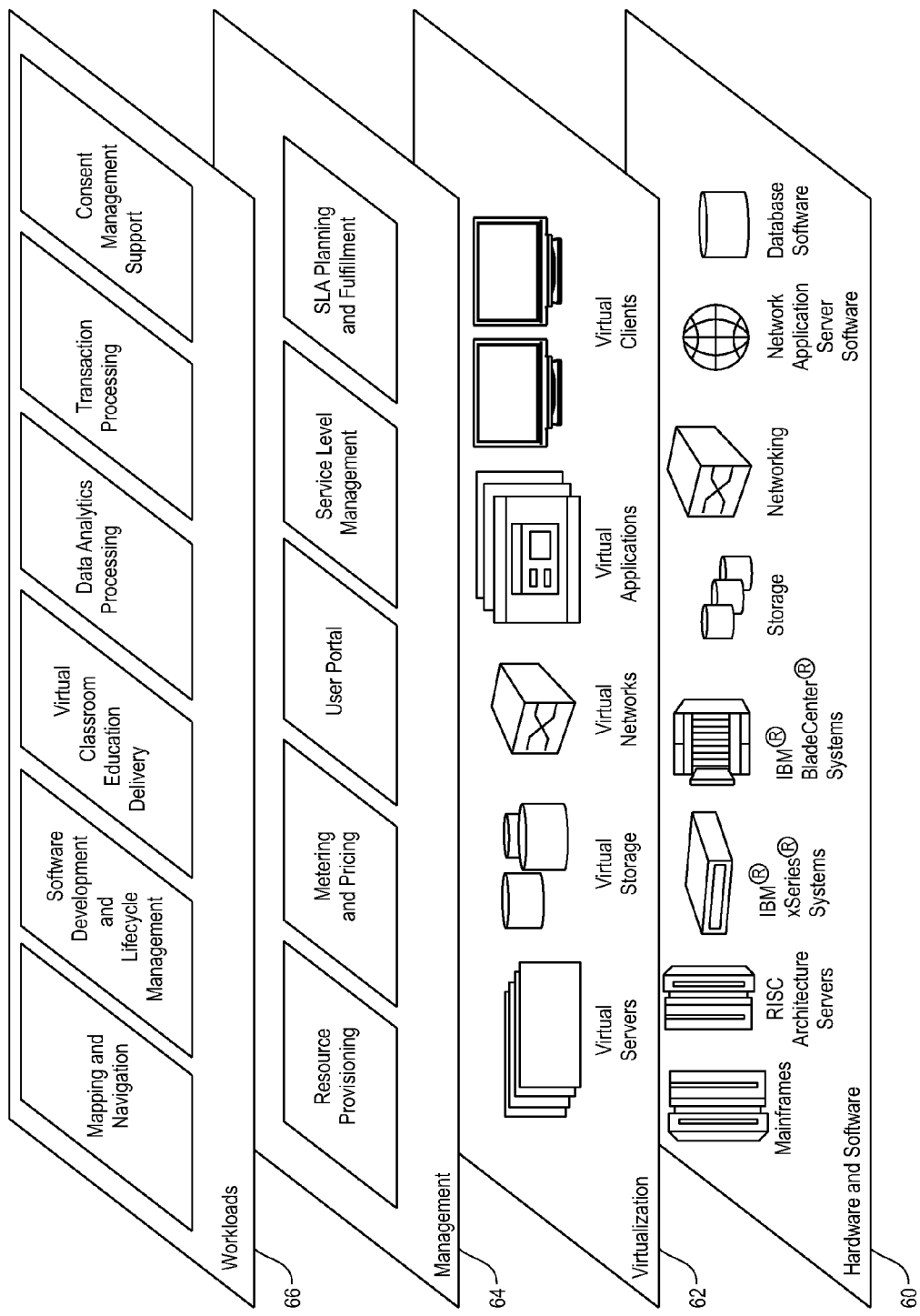
FIG. 3 depicts abstraction model layers according to an embodiment of the present invention.

Referring now to FIG. 3, a set of functional abstraction layers provided by cloud computing environment (50) is shown. It should be understood in advance that the components, layers, and functions shown in FIG. 3 are intended to be illustrative only and embodiments of the invention are not limited thereto. As depicted, the following layers and corresponding functions are provided: hardware and software layer (60), virtualization layer (62), management layer (64), and workload layer (66). The hardware and software layer (60) includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer (62) provides an abstraction layer from which the following examples of virtual entities may be provided: virtual servers; virtual storage; virtual networks, including virtual private networks; virtual applications and operating systems; and virtual clients.

In one example, management layer (64) may provide the following functions: resource provisioning, metering and pricing, user portal, service level management, and SLA planning and fulfillment. The functions are described below. Resource provisioning provides dynamic procurement of computing resources and other resources that are utilized to perform tasks within the cloud computing environment. Metering and pricing provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer (66) provides examples of functionality for which the cloud computing environment may be utilized. Examples of workloads and functions which may be provided from this layer includes, but is not limited to: mapping and navigation; software development and lifecycle management; virtual classroom education delivery; data analytics processing; operation processing; and maintenance of data security to support decision making and associated consent management within the cloud computing environment.

In the shared pool of configurable computer resources described herein, hereinafter referred to as a cloud computing environment, files may be shared among users within multiple data centers, also referred to herein as data sites. A series of mechanisms are provided within the shared pool to provide decision making controls for access to one or more records based upon associated record access and inherent characteristics of privacy. Three knowledge bases are employed with respect to consent management, including importance, sensitivity, and relevance. Analytical techniques employ the knowledge bases to assist with making access control decisions.

Figure 4:
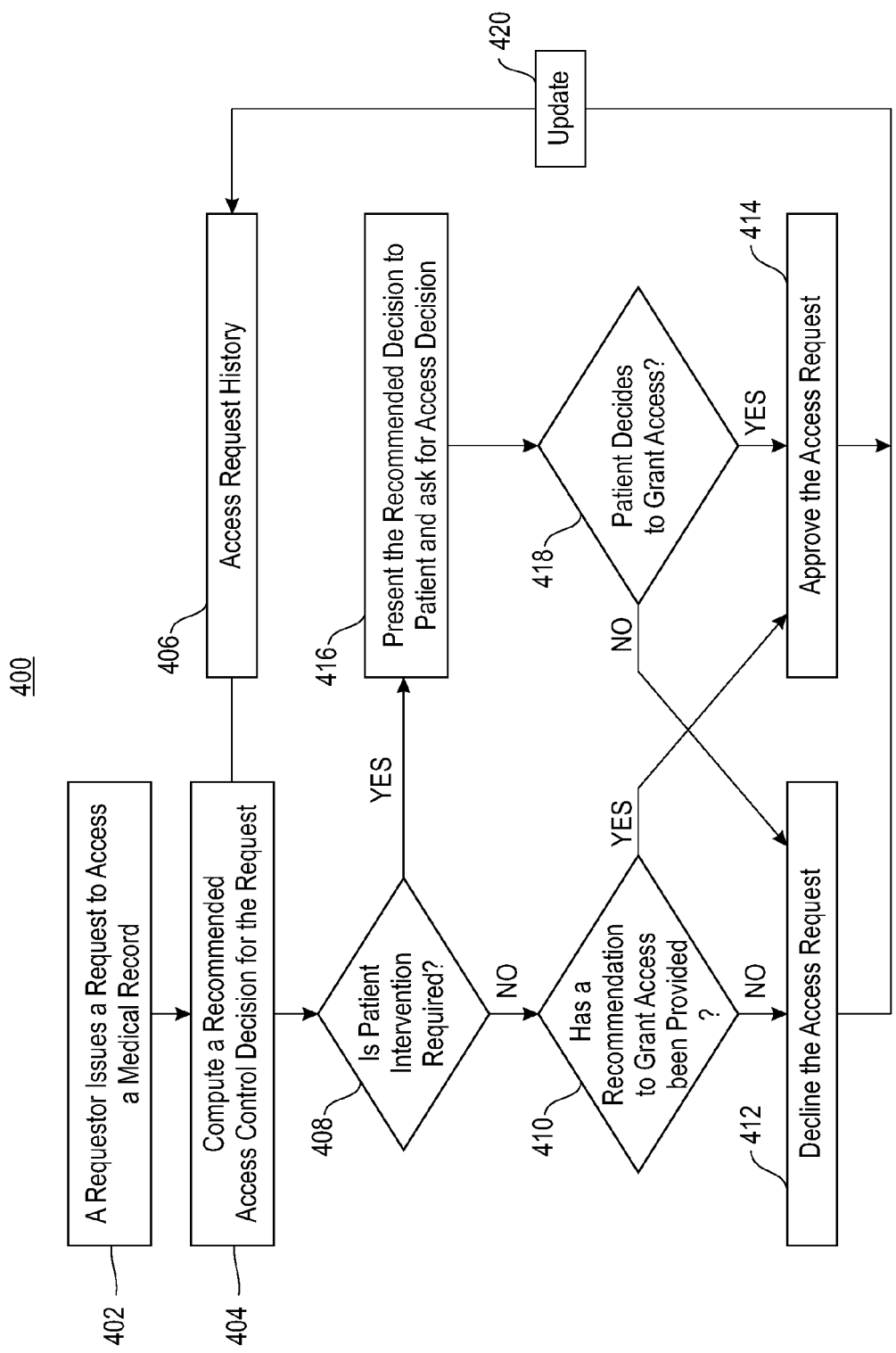
FIG. 4 depicts a flow chart illustrating a process for consent management to access one or more private records.

FIG. 4 is a flow chart (400) illustrating a process for consent management to access one or more private records. For illustrative purposes, the description pertains to medical records of a patient. However, the invention should not be limited to medical records, and in one embodiment, the invention may apply to any records available in a shared resource environment. As shown, a requestor issues a request to access a medical record of a patient (402). In one embodiment, the request may be accompanied with a specific purpose for the record request. Responsive to the request, a recommended access control decision is computed (404). Details of the computation are shown in FIGS. 5-9. As shown herein, input into the computation at step (404) is provided by a history of record request(s) (406). Following step (404), it is determined if patient intervention is required to address the record request (408). Similarly, following a negative response to the determination at step (408) it is determined if a recommendation to grant access to the requested record has been provided (410). A negative response to the determination at step (410) is followed by declining access to the requested record (412). Conversely, a positive response to the determination at step (410) is following by approving access to the requested record (414). Accordingly, if it is determined that patient intervention is not required and/or solicited for the access request, the access request is based upon the computed recommended access control decision.

If at step (408) it is determined that patient intervention is required to address the record request, the computed recommended decision is presented to the patient (416) and the patient is requested to provide a decision about access to the requested record (418). The patient may either grant or deny access to the requestor. A grant of access is followed by proceeding to step (414), whereas a denial of access is followed by proceeding to step (412). Whether the request has been granted or denied based upon patient intervention, or not, the decision is maintained in a data structure containing a history of record request(s) (406), which is updated (420) following either step (412) or (414). As noted above, past access decisions to a record are a factor in future computation of access control decisions.

Figure 5:
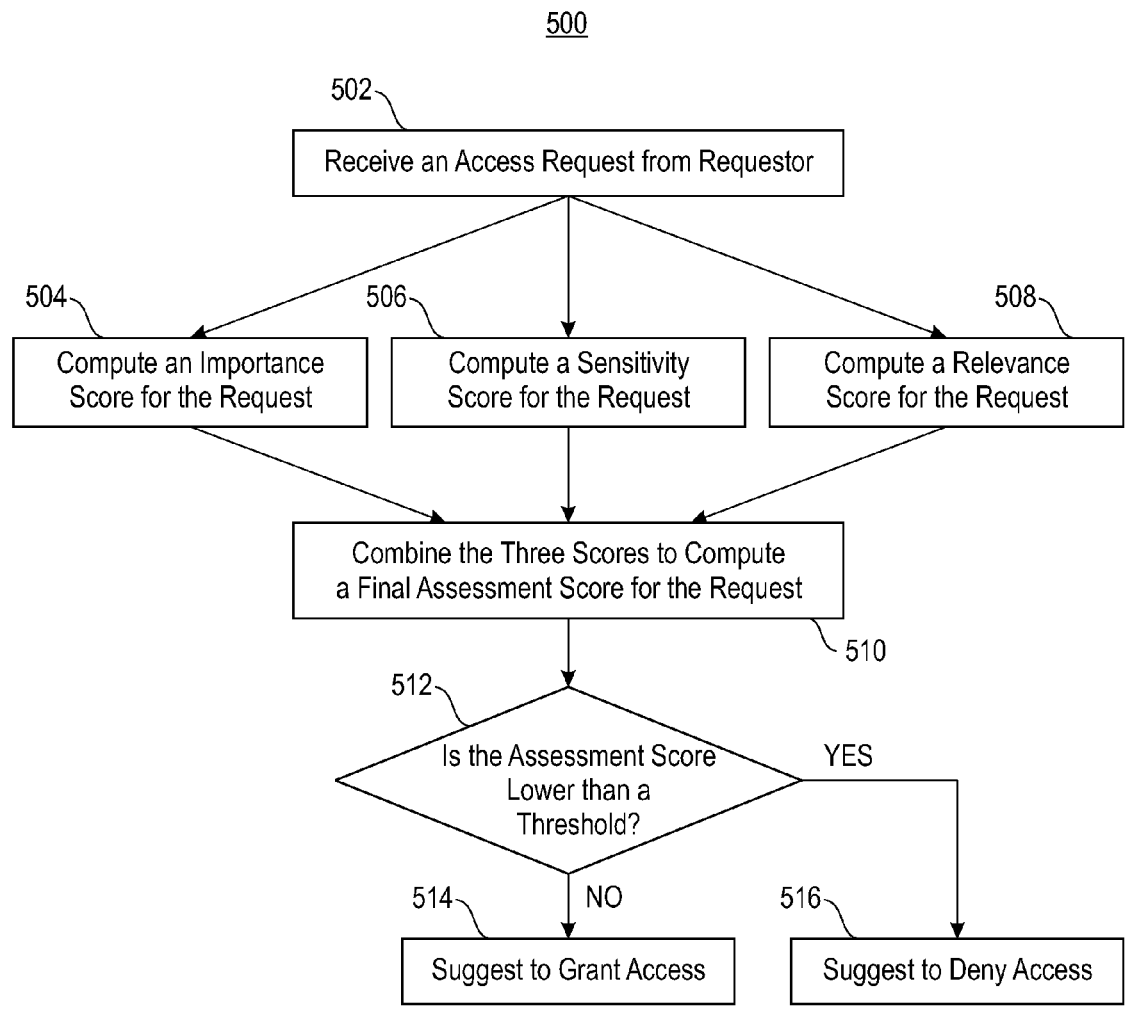
FIG. 5 depicts a flow chart elaborating on the computation of the final assessment score and the associated factors.
Figure 6:
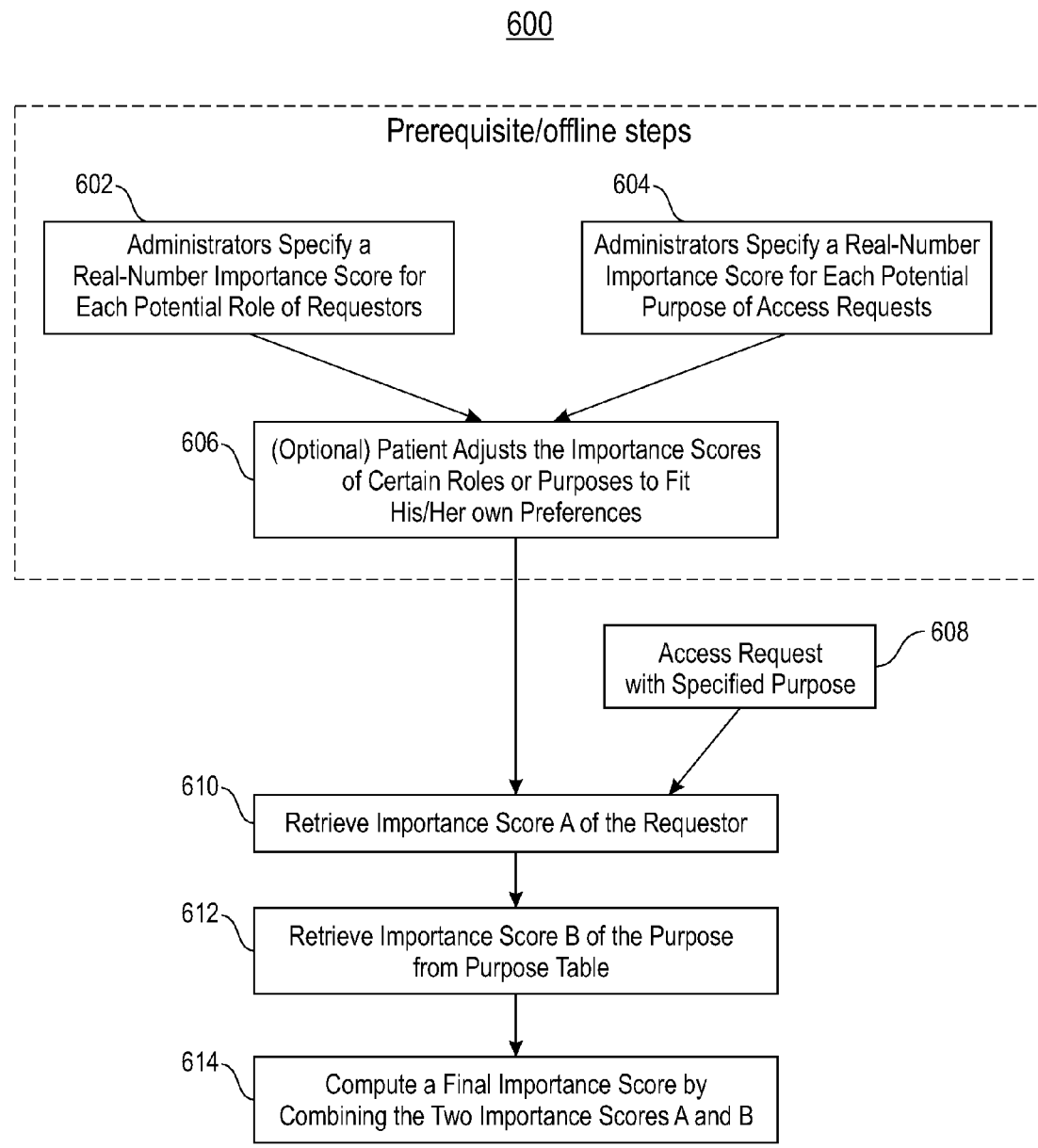
FIG. 6 depicts a flow chart illustrating a process for computing the importance score.
Figure 7:
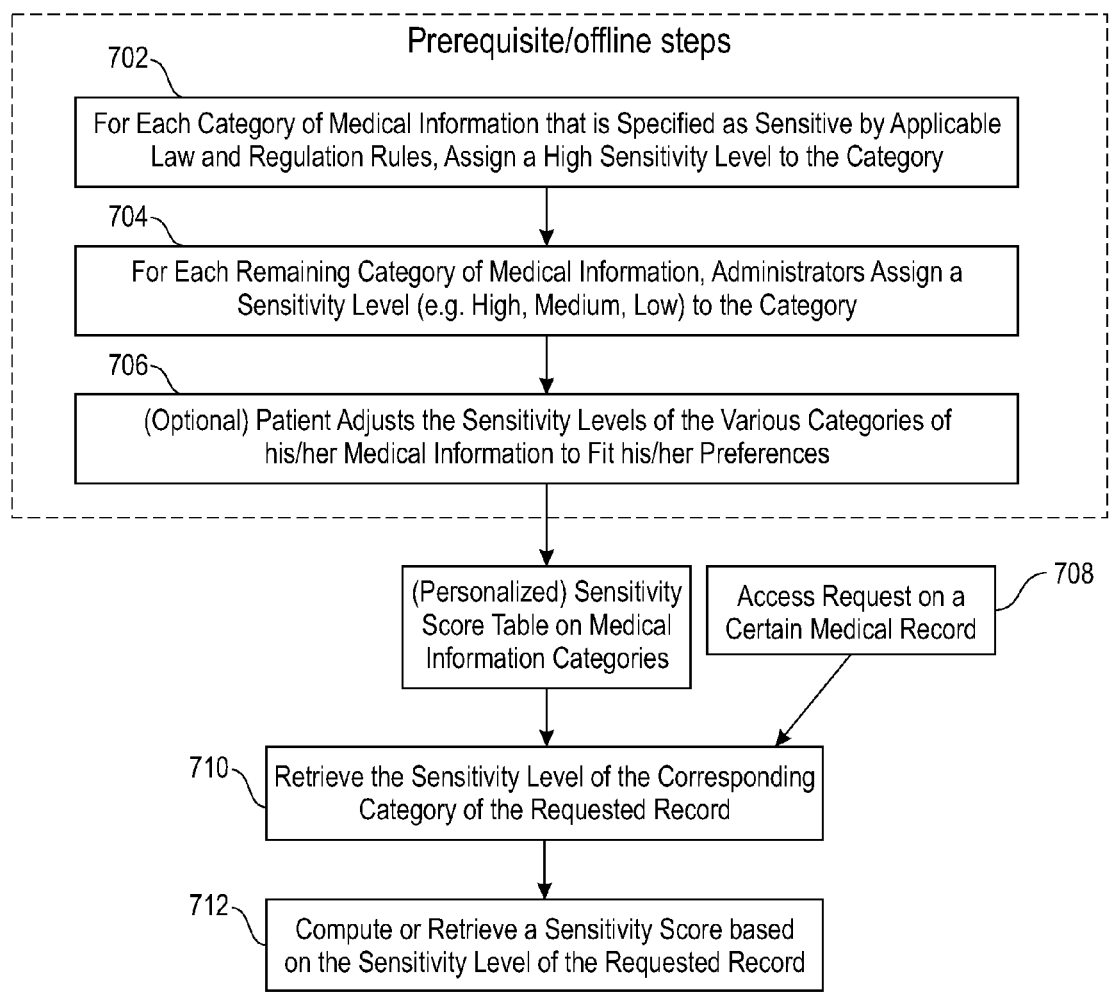
FIG. 7 depicts a flow chart illustrating a process for computing a sensitivity score.
Figure 8:
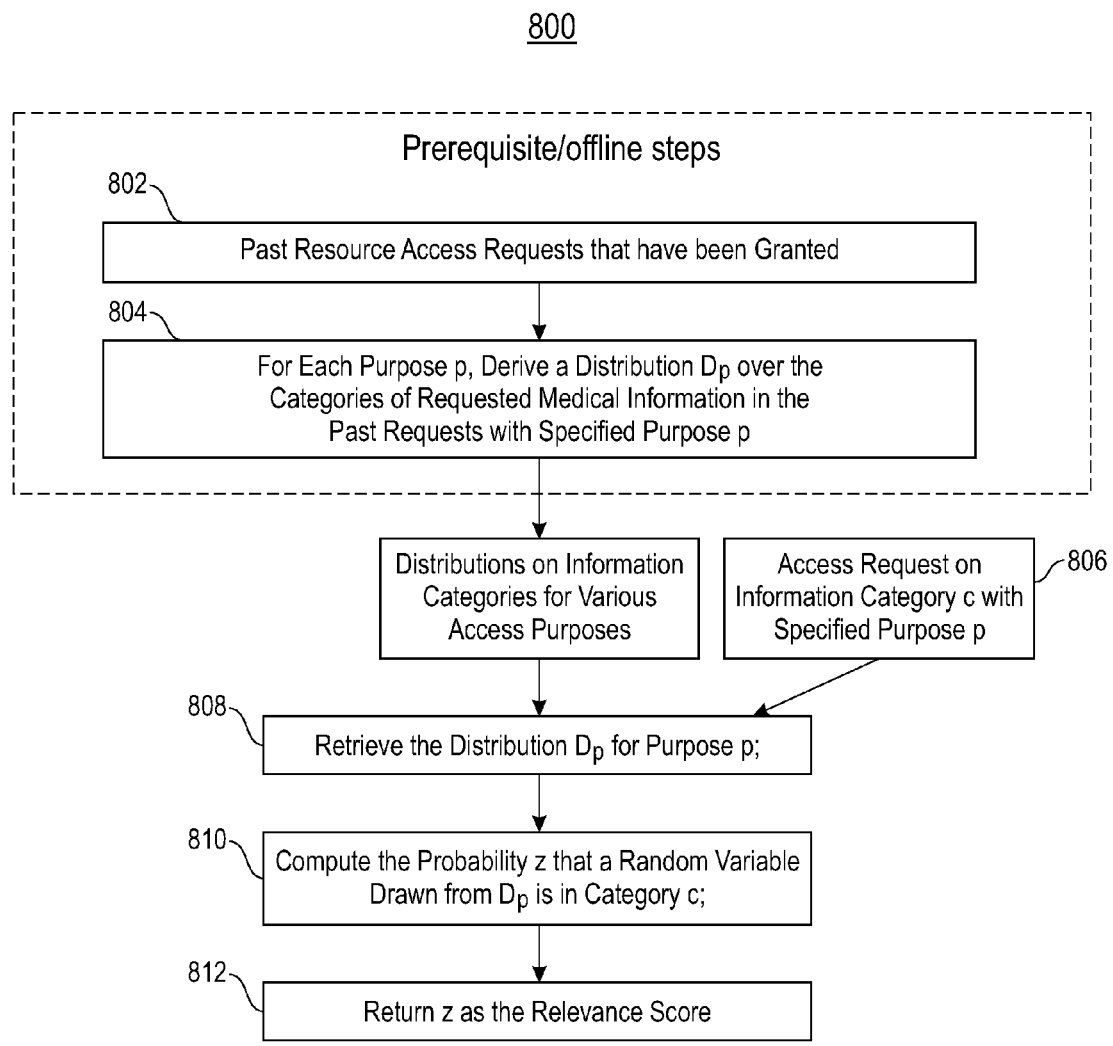
FIG. 8 depicts is a flow chart illustrating a process for computing a relevance score.

As explained briefly above, there are three factors that are employed in the computation for an access control decision, including importance, sensitivity, and relevance. FIG. 5 is a flow chart (500) elaborating on the computation at step (404) and the three factors. More specifically, an access request to a record is received from a requestor (502). Based upon the access request, the following scores are calculated: importance (504), sensitivity (506), and relevance (508). Details of the importance score are shown in FIG. 6, details of the sensitivity score are shown in FIG. 7, and details of the relevance score are shown in FIG. 8. These three scores are combined to compute a final assessment score for the request (510). In one embodiment, prior to the computation of the final assessment score, the user may provide feedback regarding the current requestor with the feedback employed as a factor in the final assessment score. For example, the feedback may be a numerical value as follows: greater than one if the patient trusts the requestor, a zero value if the patient is neutral, and a negative value if the patient does not trust the requestor. In one embodiment, the feedback value is combined with the importance, sensitivity, and relevance scores. For example, in one embodiment, the geometric mean of the importance, sensitivity, and relevance scores may be computed followed by a product of the geometric mean and the user feedback score. Accordingly, the final assessment score may mathematically combine user feedback.

Following step (510), it is determined if the assessment score is lower than a set threshold (512). A negative response to the determination at step (512) is followed by a recommendation to grant access to the record request (514), and a positive response to the determination at step (512) is followed by a suggestion to deny access to the requested record (516). In one embodiment, the threshold comparison at step (512) may be inverted; accordingly, the invention should not be limited to the specific embodiment illustrated herein. Details of the threshold calculation and determination are shown below in FIG. 9. Accordingly, a plurality of factors is employed to assess whether the record request should be enabled or denied.

One of the scores employed in the recommendation process is the importance score. The importance score is a function of the requestor identity and the purpose of the access request. FIG. 6 is a flow chart (600) illustrating a process for computing the importance score. More specifically, a real number score is provided for each requestor based upon the role of the requestor (602). In one embodiment, an administrator specifies a real number value for each requestor. In addition, a real number score is provided for each potential purpose of an access request (604). For example, in one embodiment there may be a list categorizing access requests that may be selected, and each access request is provided a score pertaining to the purpose of the request. The importance measure may be pre-defined by an administrator and/or automatically computed based on a current medical condition of a patient. In one embodiment, the administrator may specify that the importance level of emergent care is high, daily medical care is medium, and secondary usage of medical records, such as research and/or advertisement, is low. Similarly, in one embodiment, the medical condition of a patient may be employed as an input value to evaluate the severity of a situation with a numerical score pertaining to the importance of the medical condition as output. In another embodiment, a request from a physician may be classified at a higher priority level than a medical administrator. In addition to the scores of importance associated with the administrators and the purpose of the request, as shown at steps (602) and (604), respectively, the patient may optionally adjust the importance scores pertaining to specific roles and/or purposes based upon personal preferences (606). Accordingly, at least two importance scores associated with a record request are employed as input.

Given an access request to a specific record, a final importance score is computed by combining the role importance with the purpose importance. As shown, input is received from steps (602) and (604), and optionally step (606), as well as input associated with the access request with a specified purpose (608). In one embodiment, the importance scores from steps (602) and (604) are maintained in a data structure and retrieved in response to an access request. More specifically, an importance score pertaining to the role of the requestor is retrieved (610) and an importance score pertaining to the purpose of the request is retrieved (612). The two retrieved scores are mathematically or logically combined to compute a final importance score (614). Accordingly, the numerical values assigned to the role and the purpose of the request is combined to attain a single value associated with the importance level associated with the record request.

In addition to assessing the importance characteristic of the medical record, the sensitivity of the record is also assessed. Sensitivity is a different characteristic than importance. More specifically, sensitivity is customized and personalized. In one embodiment, sensitivity may be based upon a legal standard and definition and/or a patent identification of sensitive matter. FIG. 7 is a flow chart (700) illustrating a process for computing a sensitivity score. As shown, for each category of medical information that is specified as sensitive by applicable law and/or regulation, a high sensitivity level is assigned to the category (702). Similarly, for each category of medical information that is not specified by law and/or rules as sensitive, an administrator assigned a sensitivity level (704). Optionally, the patient may provide an adjustment to the sensitivity levels to one or more categories of their own medical information based upon personal preference (706).

In response to an access request for a specified medical record (708), the sensitivity level of the corresponding category of the requested record is retrieved (710). In one embodiment, the sensitivity level is retrieved based upon the assigned sensitivity levels shown at steps (702)-(706). Based upon the request at step (708) and the retrieval at step (710), a sensitivity score is either retrieved or computed based on the sensitivity level of the requested record (712). Different functions may be employed to derive a sensitivity score from a sensitivity level. In one embodiment, a numerical value is assigned to each sensitivity level, and the sensitivity score is computed as $2^v$ where v is the value of the corresponding sensitivity level. Based upon this embodiment, the higher the sensitivity level the larger the sensitivity score. Other formulas may be employed to mathematically or logically compute a sensitivity score, and as such, the invention should not be limit to the embodiment shown herein. Accordingly, the sensitivity score is assessed based upon a combination of the access request and the category of the corresponding requested record.

In addition to sensitivity and importance, a relevance score associated with the requested record is assessed. Relevance is based upon past record access requests that have been approved for retrieval. FIG. 8 is a flow chart (800) illustrating a process for computing a relevance score. Past record access requests that have been granted are employed as input (802). For each purpose, p, a distribution, $D_p$, over the categories of requested medical information of past requests with specified purpose p, is derived (804). The distribution, $D_p$ computed at step (804), and an access requests for record data in category c with specified purpose p (806) are employed as input factors. More specifically, in response to the access request at step (806), the distribution $D_p$ for purpose p is retrieved (808), thereby deriving relevance information from past access activities. In one embodiment, all of the approved access requests with purpose p are retrieved and form the distribution $D_p$. The probability that a random variable drawn from the distribution $D_p$ in category c is computed (810), and returned as the relevance score (812). Accordingly, the relevance score is computed based upon a derived distribution for a specified purpose.

Different mathematical and/or logical formulations may be employed for the computation at step (812). In one embodiment, the relevance score is computed based upon the following formula:

$$f(p, c_i) = N(p, c_i) / \text{Sum}_{c_j \in C} N(p, c_j)$$

where, C is the set of all categories and $N(p, c_i)$ is the values of the counter corresponding to p and $c_i$ (that is, the number of past requests for record data in category c with specified purpose p). In one embodiment, to scale the returned score(s), the larger the returned value at step (812), the more relevant the medical record type with respect to the given purpose. Similarly, in one embodiment, the relevance is updated on a periodic basis to account for recent retrieval trends. For example, older activities may be discounted to allow for adaptation of more recent access patterns. Accordingly, the relevance score is computed based upon a distribution of historical data for a specified category.

The relevance function is updated on a periodic basis to address current trends associated with record requests and retrieval. In one embodiment, when the relevance function is updated, a list of approved access requests is integrated from the last update into statistics. In a further embodiment, an emphasis is placed on more recent activities to support adaptation to new access patterns. Accordingly, the relevance function adapts based upon recent trends.

As shown in FIG. 5, there are three elements combined for computing a final assessment score for the request, including the importance score shown in detail in FIG. 6, the sensitivity score shown in detail in FIG. 7, and the relevance score shown in FIG. 8. In one embodiment, the final assessment score is a sum of the product of each score and an associated weight computed as follows:

$$S_{final} = (w_1 \times s_{imp}) + (w_2 \times s_{sen}) + (w_3 \times s_{rel})$$

where $s_{imp}$ is the importance score, $s_{sen}$ is the sensitivity score, and $s_{rel}$ is the relevance score, and where $w_1$, $w_2$, and $w_3$ are real-number weights. In one embodiment, the weights, $w_1$, $w_2$, and $w_3$, are periodically subject to change based upon past access requests and associated decisions. Similarly, other formulas and/or weights may be employed to determining a final assessment score based upon the importance, sensitivity, and relevance scores. Accordingly, the scores and/or their associated weights are mathematically combined to provide a final assessment score that is employed in the record access determination.

Figure 9:
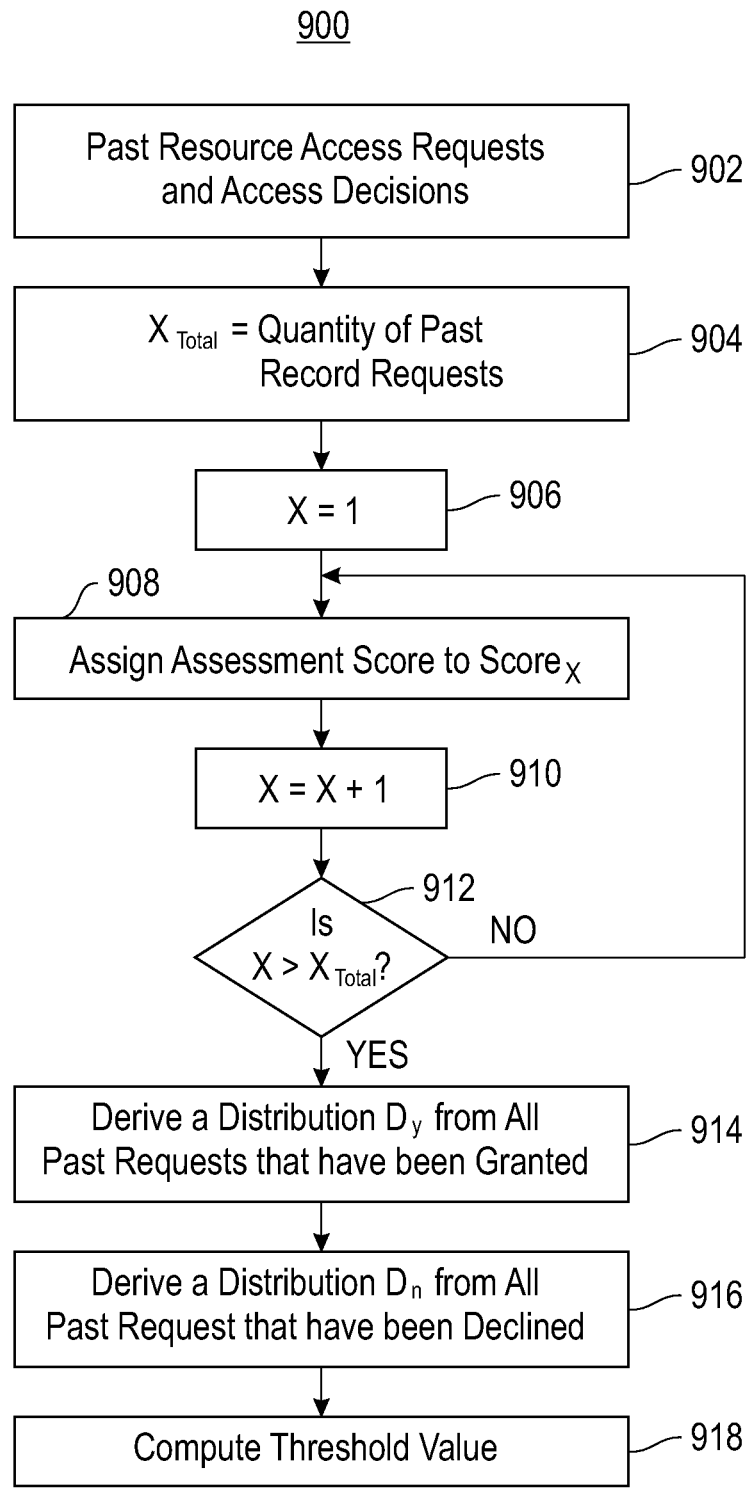
FIG. 9 depicts a flow chart illustrating a process for a process to determine a threshold value.

Once the final assessment score is computed, the final assessment score is compared with a threshold value which is further employed to enable or deny access to the requested record. FIG. 9 is a flow chart (900) illustrating a process to determine a threshold value. In one embodiment, the threshold value is not constant; rather it is a dynamic value that affects a consent recommendation to a patient. As shown, past resource access requests and associated decisions are elements reflected as input in the threshold determination (902). Each past request has an assessment score. The variable $X_{Total}$ is assigned to the quantity of past record requests (904) and an associated counting variable X is assigned to the integer one (906). For each past record request that was either granted or denied, the assessment score is assigned to the variable $score_X$ (908). Following step (908), the counting variable is incremented (910) followed by a determination of whether all of the past record requests have been evaluated (912). A negative response to the determination at step (912) is following by a return to step (908), and a positive response to the determination at step (912) concludes the evaluation process.

Two separate distributions of past assessments scores are derived. More specifically, based upon the evaluation process shown at steps (904)-(912), a distribution $D_y$ is derived from all past assessment scores, $score_X$, that have been granted (914) and a separate distribution $D_n$ is derived from all past assessment scores, $score_X$, that have been denied (916). Accordingly, the distributions derived at steps (914) and (916) provide separate comprehensive views of responses to record requests that have either been granted or denied.

Following steps (914) and (916), a threshold value is computed based upon past resource access requests and their associated decisions, either approved or denied. More specifically, the threshold value is based upon two elements of probability. First, the probability that a value randomly drawn from $D_y$ is smaller than the threshold value, T, is no larger than a pre-specified value $K_1$. In one embodiment, the function f(x) is the probability mass function of $D_y$, and the probability that a value randomly drawn from $D_y$ is smaller than T is computed based on the following formula:

$$Pr(x<T) = \int_{x<T} f(x)dx$$

The second element of probability is that a value randomly drawn from $D_n$ is larger than the threshold value, T, which is no larger than a pre-specified value $K_2$. The values of $K_1$ and $K_2$ depend on the security need and the existence of a solution value T. In one embodiment, common values of $K_1$ and $K_2$ are 0.1, 0.05, 0.01, etc. Accordingly, meeting or exceeding the threshold value is a factor in the decision to approve or decline access to the record request.

As shown in FIGS. 4-9, a mathematical assessment is employed to provide a recommendation to a patient with respect to accessing a private medical record. However, as shown in FIG. 1, the patient may be provided the final determination as to approval or denial of the access request. More specifically, the mathematical assessment provides a suggestion to the patient with regards to the access request based upon the corresponding assessment score. In one embodiment, an assessment score greater than the threshold will result in a suggestion for the patient to grant the access request, and an assessment score less than the threshold will result in a suggestion for the patient to deny the access request. The thresholds may be manually or automatically determined based on past record requests. Furthermore, the importance, sensitivity, and relevance scores may be presented to the patient so that the patient may evaluate the request and the suggested action.

Figure 10:
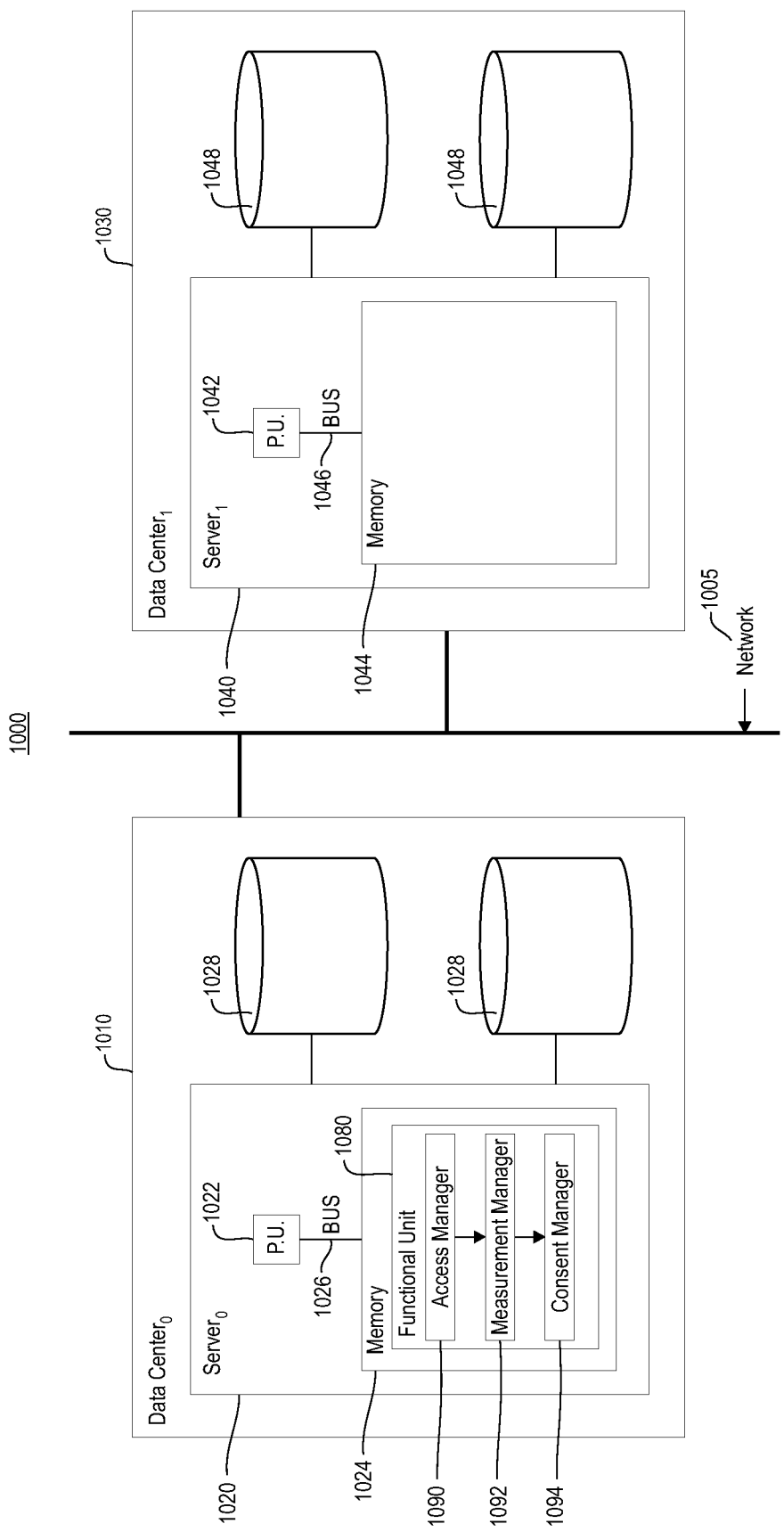
FIG. 10 depicts a block diagram illustrating tools embedded in a computer system for consent management of a record within a shared group of resources.

As shown in FIGS. 4-9 described above, a method is provided to support an adaptive consent management with respect to a record access. Access to private data records is reduced by providing an adaptive technique that accounts for factors of importance, sensitivity, and relevance, as well as input from the owner of the record. FIG. 10 is a block diagram (1000) illustrating tools embedded in a computer system to support the adaptive technique employed for determining access rights to a requested record within a shared group of resources. More specifically, a shared pool of configurable computer resources is shown with a first data center (1010) and a second data center (1030). Although two data centers are shown in the example herein, the invention should not be limited to this quantity of data centers in the computer system. Accordingly, one or more data centers may be employed to support collaboration and data leakage prevention.

Each of the data centers in the system is provided with at least one server in communication with data storage. More specifically, the first data center (1010) is provided with a server (1020) having a processing unit (1022), in communication with memory (1024) across a bus (1026), and in communication with data storage (1028); and the second data center (1030) is provided with a server (1040) having a processing unit (1042), in communication with memory (1044) across a bus (1046), and in communication with second local storage (1048). Server (1020) may communicate with server (1040) across a network connection (1005).

In the a shared pool of configurable computer resources, including the first data center (1010) and the second data center (1030), one or more files may be shared. A functional unit (1080) is provided with one or more tools to support the aspect of managing access of a shared file, and more specifically for managing consent with respect to access to the shared file. The tools include, but are not limited to, an access manager (1090), a measurement manager (1092), and a consent manager (1094). The access manager (1090) is provided in the shared pool to manage access of a shared file. As shown herein, the access manager (1090) is local to the first data center (1010). The access manager (1090) is responsible for receiving an access request to a record maintained in storage.

The access request includes identifying characteristics, including a record type and an identifier of a requestor associated with the request. The measurement manager (1092) is responsible for computing the following elements to support a consent decision associated with the access request: an importance measurement, a sensitivity measurement, and a relevance measurement. In one embodiment, the relevance measurement includes a mathematical value associated with one or more previous requests for the same record type, such as a percentage of prior record requests for the record type. Similarly, in one embodiment, the sensitivity measurement includes one of the following factors: sensitivity of the record type as mandated by law, a sensitivity level set by a patent associated with the record type, and historical data regarding the sensitivity level for the record type. Sensitivity is highly customized and personalized as different local laws may have different definitions on sensitive medical information. Accordingly, the measurement manager (1092) provides the computation support for the factors employed in determining a consent recommendation.

As described above, the measurement manager (1092) provides factors employed in the consent recommendation. More specifically, the consent manager (1094) computes a consent recommendation based upon the factors of importance, sensitivity, and relevance as provided by the measurement manager (1092). The consent manager (1094) provides a consent recommendation for the access request to the requested record. More specifically, the consent manager (1094) either grants or denies access to the requested record. In one embodiment, the consent manager (1094) computes a threshold value that reflects a probability of values drawn from a distribution of both granted and declined record access requests. This threshold value may be employed by the consent manager (1084) as a factor in the final consent recommendation.

The record described herein is retained in data storage, either local or remote. In one embodiment, the record may be a patient record, a medical record, or any form of a private record. With respect to a patient record, the consent manager (1094) decision is communicated to a patent and the patient makes the final decision. Similarly, if the record is a patient medical record, the importance measurement as computed by the measurement manager (1092) includes one of the following factors: a current condition of the subject patient, the identity of the person requesting the record, and a condition characteristic associated with the request. In one embodiment, a condition characteristic may include an administrator specifying that the importance level of emergent care is high, daily medical care is medium, and secondary usage of medical records is low. Similarly, in one embodiment, a computer program may be employed to take a patient's current medical condition as input and to automatically evaluate the severity of the situation, and to assign a condition characteristic value reflecting the current state of the medical condition.

When the record pertains to a patient medical record, the associated record access is restricted to the patient, designated family and/or friends, and appropriate medical professionals. A requestor requesting access to a medical record may be a primary requestor, such as a physician, a secondary requestor, such as a medical administrator, and non-medical personnel. In one embodiment, a numerical value is associated with the classification of the requestor and employed in the measurement factors for the consent evaluation. As explained herein, a consent recommendation is provided to either grant or deny access to a medical record. In one embodiment, a feedback adjustment score is provided from the patient and employed as a factor in the final computed assessment. Examples of a feedback adjustment score include, but are not limited to, a value greater than one if the patient trusts the requestor, a value of zero if the patient is neutral or has no feedback, and a negative value if the patient does not trust the requestor. As noted above, in one embodiment, all of the computed measurements are numerical values, and as such the feedback score is also a numerical value so as to provide a score directly from the patient owning the record. Accordingly, the access manager (1090), measurement manager (1092), and consent manager (1094) function to manage consent to access a private record based upon a numerical assessment.

The access manager (1090), measurement manager (1092), and consent manager (1094) are configured to address the complex nature of privacy associated with medical records, both from a legal and medical perspective. More specifically, each record request is individually assessed based upon the nature of the request, including the specific record and the requestor, as well as historical data associated with similar record requests. The system functions in a dynamic manner to address the ever changing characteristics of the medical community, privacy laws, medical record law, including local and non-local rules and regulations, etc. Accordingly, access manager (1090), measurement manager (1092), and consent manager (1094), address the dynamic and sensitive nature of the consent management of medical records through an individual assessment of a request, while accounting for past recommendations of the record type, and/or patient feedback.

As identified above, the access, measurement, and consent managers (1090), (1092), and (1094), respectively, are shown residing in memory (1024) of the server (1020) local to the first data center (1010). Although in one embodiment, the access, measurement, and consent managers, respectively, may reside as hardware tools external to memory (1024) of server (1020), they may be implemented as a combination of hardware and software, or may reside local to memory of the second data center (1030) in the shared pool of resources. Similarly, in one embodiment, the managers may be combined into a single functional item that incorporates the functionality of the separate items. As shown herein, each of the manager(s) are shown local to one data center. However, in one embodiment they may be collectively or individually distributed across the shared pool of configurable computer resources and function as a unit to manage dynamic file sharing collaboration while mitigating data leakage. Accordingly, the managers may be implemented as software tools, hardware tools, or a combination of software and hardware tools.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 11:
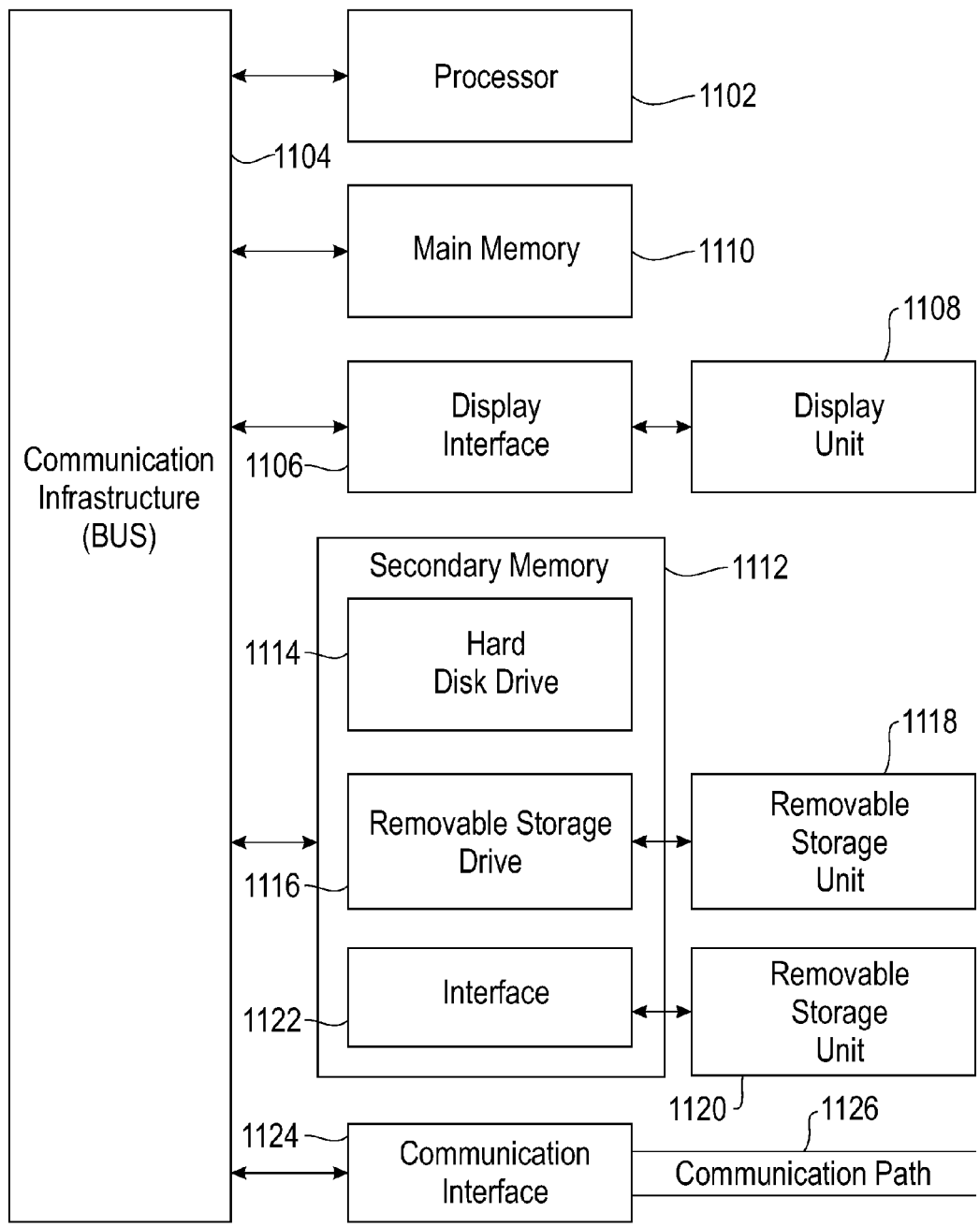
FIG. 11 depicts a block diagram showing a system for implementing an embodiment of the present invention.

Referring now to FIG. 11 is a block diagram (1100) showing a system for implementing an embodiment of the present invention. The computer system includes one or more processors, such as a processor (1102). The processor (1102) is connected to a communication infrastructure (1104) (e.g., a communications bus, cross-over bar, or network). The computer system can include a display interface (1106) that forwards graphics, text, and other data from the communication infrastructure (1104) (or from a frame buffer not shown) for display on a display unit (1108). The computer system also includes a main memory (1110), preferably random access memory (RAM), and may also include a secondary memory (1112). The secondary memory (1112) may include, for example, a hard disk drive (1114) and/or a removable storage drive (1116), representing, for example, a floppy disk drive, a magnetic tape drive, or an optical disk drive. The removable storage drive (1116) reads from and/or writes to a removable storage unit (1118) in a manner well known to those having ordinary skill in the art. Removable storage unit (1118) represents, for example, a floppy disk, a compact disc, a magnetic tape, or an optical disk, etc., which is read by and written to by removable storage drive (1116). As will be appreciated, the removable storage unit (1118) includes a computer readable medium having stored therein computer software and/or data.

In alternative embodiments, the secondary memory (1112) may include other similar means for allowing computer programs or other instructions to be loaded into the computer system. Such means may include, for example, a removable storage unit (1120) and an interface (1122). Examples of such means may include a program package and package interface (such as that found in video game devices), a removable memory chip (such as an EPROM, or PROM) and associated socket, and other removable storage units (1120) and interfaces (1122) which allow software and data to be transferred from the removable storage unit (1120) to the computer system.

The computer system may also include a communications interface (1124). Communications interface (1124) allows software and data to be transferred between the computer system and external devices. Examples of communications interface (1124) may include a modem, a network interface (such as an Ethernet card), a communications port, or a PCM-CIA slot and card, etc. Software and data transferred via communications interface (1124) are in the form of signals which may be, for example, electronic, electromagnetic, optical, or other signals capable of being received by communications interface (1124). These signals are provided to communications interface (1124) via a communications path (i.e., channel) (1126). This communications path (1126) carries signals and may be implemented using wire or cable, fiber optics, a phone line, a cellular phone link, a radio frequency (RF) link, and/or other communication channels.

In this document, the terms "computer program medium," "computer usable medium," and "computer readable medium" are used to generally refer to media such as main memory (1110) and secondary memory (1112), removable storage drive (1116), and a hard disk installed in hard disk drive (1114).

Computer programs (also called computer control logic) are stored in main memory (1110) and/or secondary memory (1112). Computer programs may also be received via a communication interface (1124). Such computer programs, when run, enable the computer system to perform the features of the present invention as discussed herein. In particular, the computer programs, when run, enable the processor (1102) to perform the features of the computer system. Accordingly, such computer programs represent controllers of the computer system.

The flowcharts and block diagrams in the Figures illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated. Accordingly, the enhanced cloud computing model supports flexibility with respect to application processing and disaster recovery, including, but not limited to, supporting separation of the location of the data from the application location and selection of an appropriate recovery site.

Alternative Embodiment

It will be appreciated that, although specific embodiments of the invention have been described herein for purposes of illustration, various modifications may be made without departing from the spirit and scope of the invention. In particular, the system can be configured to provide consent management of other elements within a computer system, including but not limited to, any record considered confidential and/or secure, in which a user wants to enable limited sharing. Accordingly, the scope of protection of this invention is limited only by the following claims and their equivalents.

We claim:

1. A computer program product comprising a computer readable storage device having computer readable program code embodied therewith, the computer readable program code comprising:
   computer readable program code configured to receive an access request for a record;
   computer readable program code configured to identify information associated with the record and the access request, including record type, an identity of a requestor, and a purpose associated with the access request;
   computer readable program code configured to compute an importance measurement for the access request;
   computer readable program code configured to compute a sensitivity measurement for the access request;
   computer readable program code configured to compute a threshold value reflecting probability of values drawn from a distribution from granted requests and a distribution from declined requests, and employing the threshold value as a factor in the consent recommendation;
   computer readable program code configured to compute a relevance measurement for the access request, including determining a mathematical value associated with any previous requests on a same purpose for the record type; and
   computer readable program code configured to compute a consent recommendation based upon the computed importance measurement, sensitivity measurement, relevance measurement, and threshold value;
   the consent recommendation for the access request for the record, including a decision selected from the group consisting of: granting access to the requested record and denying access to the requested record;
   wherein the computer readable program code is stored on a memory storage device.

2. The computer program product of claim 1, wherein the record is a patient record, and further comprising computer readable program code configured to present the consent recommendation to the patient for the final decision.

3. The computer program product of claim 1, wherein the record is a medical record and the importance measurement includes a factor selected from the group consisting of: a current condition of a patient associated with the medical record, the requestor identity, and a condition characteristic associated with the access request.

4. The computer program product of claim 1, wherein the sensitivity measurement includes a factor selected from the group consisting of: sensitivity of the record type as mandated by law, a sensitivity level set by a patent associated with the record type, and historical data regarding the sensitivity level for the record type.

5. The computer program product of claim 1, wherein the computer readable program code configured to compute the relevance measurement for the access request includes program code to determine a percentage of prior record requests for the record type.

6. A system comprising:
   a server having a processing unit in communication with memory;
   the server in communication with a storage component that includes a data in the form of a record and information describing an access control policy to the record;
   a functional unit in communication with the storage component, the functional unit comprising:
      an access manager in communication with the storage component, the access manager to receive an access request for the record, with the access request including record type, an identity of a requestor, and a purpose associated with the access request;
      a measurement manager in communication with the access manager, the measurement manager to compute:
         an importance measurement for the access request;
         a sensitivity measurement for the access request;
         a relevance measurement for the access request, the relevance measurement including a mathematical value associated with any previous requests on a same purpose for the record type; and
      a consent manager to compute a threshold value reflecting probability of values drawn from a distribution from granted requests and a distribution from declined requests, and employing the threshold value as a factor in the consent recommendation;
      the consent manager in communication with the measurement manager, the consent manager to compute a consent recommendation based upon the computed importance measurement, sensitivity measurement, relevance measurement, and threshold value; and
      the consent recommendation for the access request for the record including a decision selected from the group consisting of: granting access to the requested record and denying access to the requested record.

7. The system of claim 6, wherein the record is a patient record, and further comprising the consent manager to present the consent recommendation to the patient for the final decision.

8. The system of claim 6, wherein the record is a medical record and the importance measurement includes a factor selected from the group consisting of: a current condition of a patient associated with the medical record, the requestor identity, and a condition characteristic associated with the access request.

9. The system of claim 6, wherein the sensitivity measurement includes a factor selected from the group consisting of: sensitivity of the record type as mandated by law, a sensitivity level set by a patent associated with the record type, and historical data regarding the sensitivity level for the record type.

10. The system of claim 6, wherein measurement manager computation of the relevance measurement for the access request includes determining a percentage of prior record requests for the record type.

11. The computer program of claim 1, further comprising associating a weight with each measurement for the access request.

12. The system of claim 6, further comprising a weight associated with each measurement for the access request.

* * * * *